US00PP35089P2

(12) United States Plant Patent
Ronald

(10) Patent No.: US PP35,089 P2
(45) Date of Patent: Apr. 11, 2023

(54) CRABAPPLE PLANT NAMED 'JEFNITE'

(50) Latin Name: ***Malus* x *adstringens***
Varietal Denomination: Jefnite

(71) Applicant: Jeffries Nurseries Ltd, Portage la Prairie (CA)

(72) Inventor: Wilbert Ronald, Portage la Prairie (CA)

(73) Assignee: JEFFRIES NURSERIES LTD, Portage la Prairie (CA)

( * ) Notice: Subject to any disclaimer, the term of this patent is extended or adjusted under 35 U.S.C. 154(b) by 0 days.

(21) Appl. No.: 17/724,644

(22) Filed: Apr. 20, 2022

Related U.S. Application Data

(60) Provisional application No. 63/181,944, filed on Apr. 29, 2021.

(51) Int. Cl.
*A01H 5/04* (2018.01)
*A01H 6/74* (2018.01)

(52) U.S. Cl.
USPC ..... Plt./173
CPC ..... *A01H 6/74* (2018.05)

(58) Field of Classification Search
USPC ..... Plt./173
CPC ..... A01H 6/74
See application file for complete search history.

(56) References Cited

PUBLICATIONS

UPOV hit to crabapple tree named, 'Jefnite', CA PBR 20-10120, published Apr. 30, 2020.*

* cited by examiner

*Primary Examiner* — Anne Marie Grunberg
(74) *Attorney, Agent, or Firm* — Penny J Aguirre

(57) ABSTRACT

A new and distinctive cultivar of flowering crabapple, botanically known as *Malus* x *adstringens* 'Jefnite', that is characterized by its narrow columnar plant habit and its glossy foliage that is purple in color all summer and fall.

3 Drawing Sheets

Botanical classification: *Malus* x *adstringens*.
Variety denomination: 'Jefnite'.

BACKGROUND OF THE INVENTION

The present invention relates to a new and distinct cultivar of *Malus* x *adstringens* and will be referred to hereafter by its cultivar name, 'Jefnite'. 'Jefnite' is a deciduous tree grown for use as an ornamental landscape plant.

The new *Malus* arose from a breeding program conducted by the Inventor at a nursery in Portage la Prairie, Manitoba, Canada. The objective of the breeding program was to develop a new cultivar of *Malus* with a columnar plant habit, disease resistance, dark purple foliage, and reduced fruit size.

The new *Malus* originated from open pollination of *Malus* 'Jefspire' (not patented) in 2008. The male parent is therefore unknown. 'Jefnite' was selected as a unique single plant derived from the resulting seedlings of the open pollination in 2011.

Asexual propagation of the new cultivar was first accomplished by vegetative budding in August of 2010 under the direction of the Inventor in Portage la Prairie, Manitoba, Canada. Asexual propagation by vegetative budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jefnite' as a unique cultivar of *Malus*.

1. 'Jefnite' exhibits a narrow columnar plant habit.
2. 'Jefnite' exhibits glossy foliage that is purple in color all summer and fall.

The female parent of 'Jefnite' differs from 'Jefnite' in having foliage that is bronze-green in color until late summer, fruit that is larger in size, and less flowers. 'Jefnite' can also be compared to the cultivars 'Jefgreen' (U.S. Plant Pat. No. 23,863) and 'JFS KW213MX' (U.S. Plant Pat. No. 31,008). 'Jefgreen' and 'JFS KW213MX' are both similar to 'Jefnite' in having a columnar habit and spring flowers that are pink in color. 'Jefgreen' differs from 'Jefnite' in having bronze-green foliage colors in spring becoming green in color in summer and a less narrow columnar habit. 'JFS KW213MX' differs from 'Jefnite' in having bronze-green foliage colors in spring becoming green in color in summer, fruit that is smaller in size, and a less narrow columnar habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on websites by ISSUU, Jeffries Nurseries, Broderick Gardens, Cheyenne Tree Farm, Zosel Tree Farm, Winnipeg Free Press, Green Tree Agroforestry Solutions, Prairie Gardens, Green Haven Garden, and Trees and Shrubs online, Sun Star Nurseries, Morden Nurseries, and Falk Nurseries.

BRIEF DESCRIPTION OF THE DRAWING

The accompanying color photographs illustrate the overall appearance and distinct characteristics of the new *Malus* as grown outdoors in a trial garden in Portage la Prairie, Manitoba, Canada. The plants in the photograph in FIG. 1 and FIG. 2 are 5 years in age and the plants in FIG. 3 is 2 years in age.

The photograph in FIG. 1 provides a view of the narrow columnar plant habit of 'Jefnite'.

Figure 1:
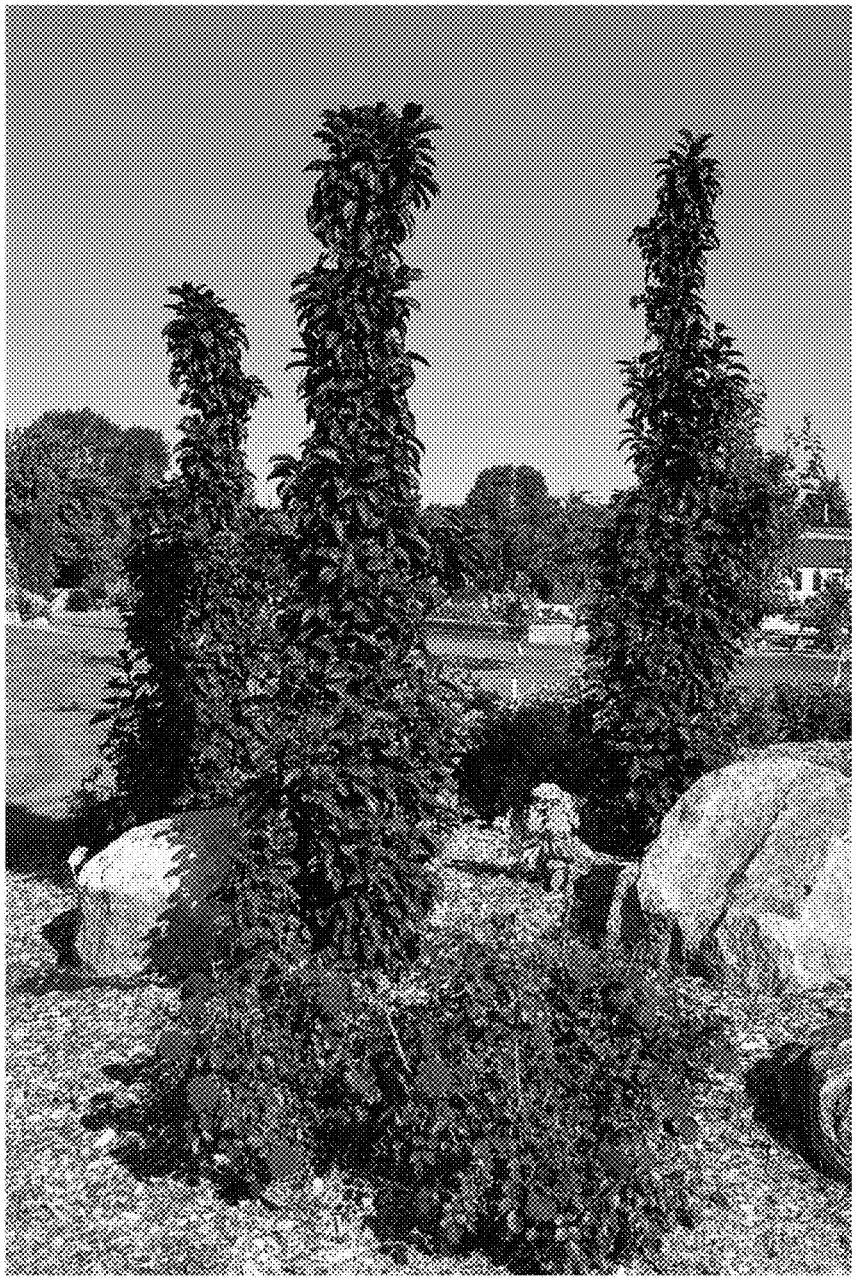
Figure 2:
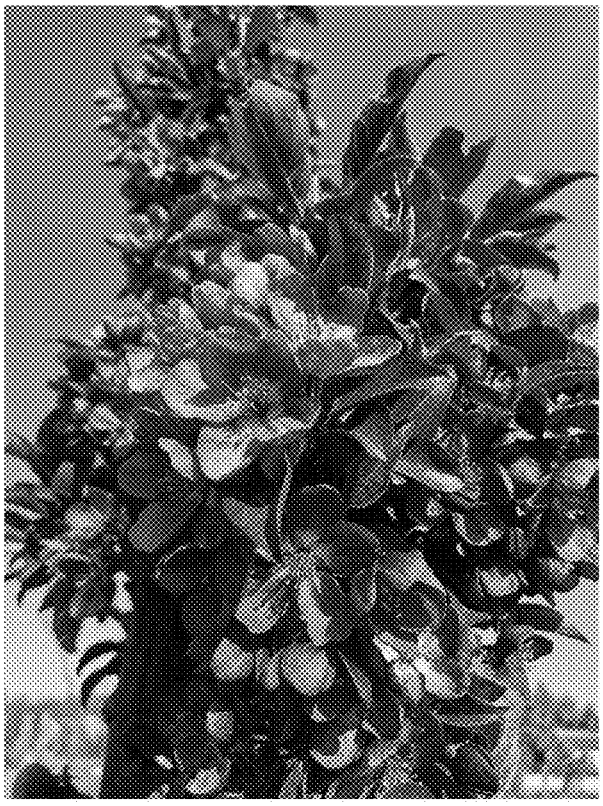

The photograph in FIG. 2 provides a close-up view of the flowers of 'Jefnite'.

Figure 3:
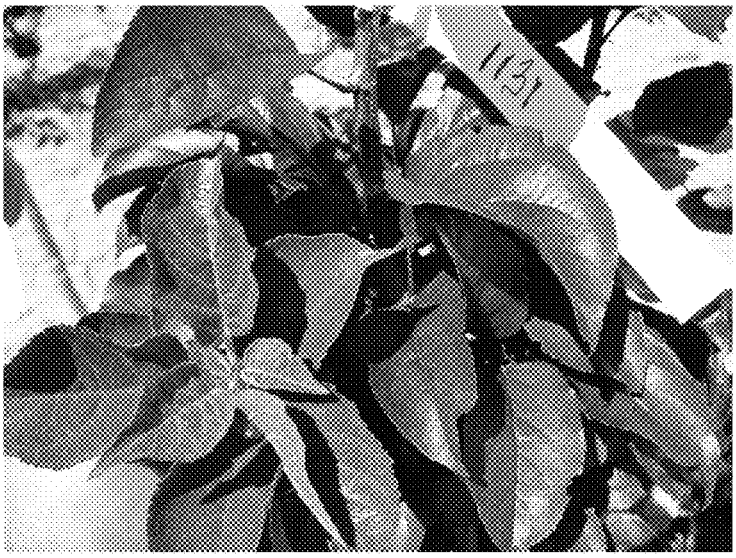

The photograph in FIG. 3 provides a close-up view of the foliage of 'Jefnite' on the right and 'Jefspire' on the left.

Figure 4:
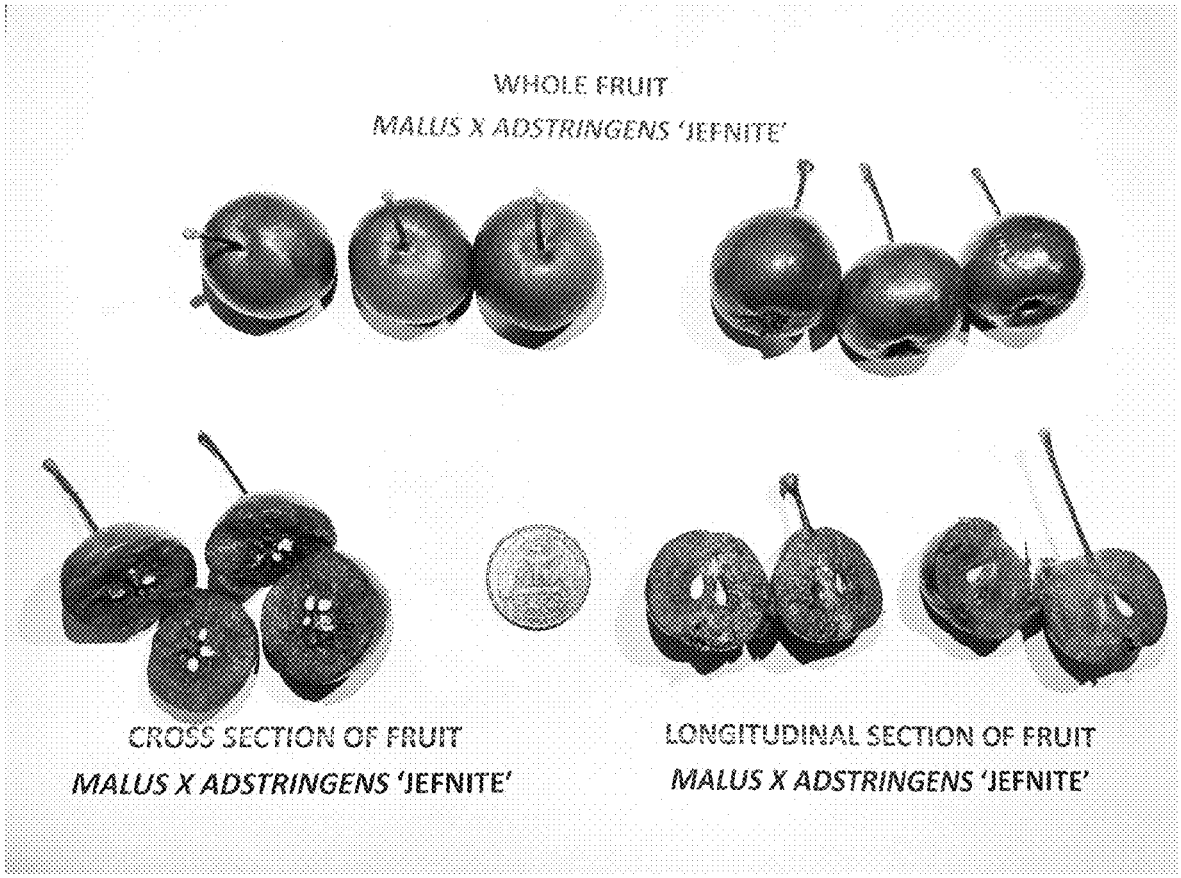

The photograph in FIG. 4 provides a view of the whole fruit (top), fruit cut longitudinally (bottom right), and fruit cut horizontally (bottom left).

The colors in the photographs may differ slightly from the color values cited in the detailed botanical description, which accurately describe the colors of the new *Malus*.

DETAILED BOTANICAL DESCRIPTION

The following is a detailed description of five-year-old trees of 'Jefnite' budded onto *Malus* rootstock and grown in a trial plot in Portage la Prairie, Manitoba, Canada. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Plant type.*—Deciduous tree.

*Tree habit.*—Narrowly columnar.

*Height and spread.*—Average of 6 m in height and 1.8 m in diameter in the landscape as a 5-year-old tree.

*Diseases and pests.*—Good resistance to apple scab (caused by *Venturia inaequalis*) and fireblight (caused by *Erwinia amylovora*), no viruses found to date, and no resistance or susceptibility to pests has been observed.

*Cold hardiness.*—At least in U.S.D.A. Zone 2.

*Propagation*—Budding onto *Malus* rootstock.

*Root development.*—About 3 weeks to bud onto rootstock and about 5 months to finish a young plant.

*Growth rate.*—Vigorous.

Branches:

*Branching habit.*—1 vertical main branch, 1 to 2 secondary stems, strong, upright branches held at an angle of about 70° to the main stem.

*Branch internode length.*—4.5 cm.

*Branch shape.*—Round.

*Branch strength.*—Strong.

*Branch size.*—An average of 92 cm in length and 1.5 cm in width, 2 year growth 21 cm, trunk 3 cm in diameter.

*Branch surface.*—New emerging growth; densely covered with woolly pubescence NN155B, younger stems and mature stems; smooth, glossy and moderately covered with round lenticels and average of 10 per sq cm, 0.2 mm in diameter, 162A in color, older bark; bark is a blend of 200A and 177B in color with lenticels; about 20 per 7 sq cm, 165B in color, about 1 mm in length and 0.4 mm in width.

*Trunk.*—4 cm in diameter 14 cm above soil level, 201A to 201B in color, lenticels oblong and narrow, 3 mm in length, horizontal, 199A in color, moderately to sparse in density; an average of 15 per 1 cm section.

*Vegetative buds.*—Conical in shape, pointed apex, an average of 5 mm in length and 4 mm in diameter at the widest point, glossy surface and 200B in color, alternate position in relation to buds with an average of 1.5 cm in length between shoots and vegetative buds.

Leaf description:

*Leaf orientation.*—Horizontal.

*Leaf division.*—Simple.

*Leaf shape.*—Elliptic.

*Leaf size.*—Average of 10 cm in length and 6.5 cm in width.

*Leaf apex.*—Acuminate.

*Leaf base.*—Cuneate to oblique.

*Leaf surface.*—Both surfaces glossy, emerging and young leaves densely covered with woolly hairs 161B in color, mature leaves sparsely covered with short stiff hairs, NN155C in color, 0.3 mm in length.

*Leaf margin.*—Serrate, moderately undulated.

*Leaf blade profile in cross-section.*—Concave.Leaf internode length — Average of 5 cm.

*Leaf color.*—Emerging; upper and lower surface 175A, young upper surface; NN137A, young lower surface; 148A, mature upper surface; 203A, mature lower surface; 148A, fall upper surface; 46A and a blend of N186A and 187A, fall lower surface; 197A, lightly flushed with 183A.

*Leaf venation.*—Pinnate, upper and lower surface 184A.

*Petioles.*—Average of 4 cm in length and 1 mm in diameter, 187A in color, surface densely covered with woolly hairs 195A in color.

*Stipules.*—147A in color, an average of 1 cm in length and 2 mm in width, glossy surfaces.

Flower description:

*Bloom period.*—May in Manitoba, Canada, typical crabapple blooming time.

*Typical bloom from year to year.*—Annual consistent blooming; primarily on spurs.

*Lastingness of flowers.*—About 10 days.

*Number of flowers.*—Average of 5 per corymb.

*Inflorescence type.*—Corymb of rotate flowers.

*Inflorescence size (corymb).*—An average of 14 cm in length and 10 cm in width.

*Flower buds.*—59A in color prior to opening, round in shape, average of 1.8 cm in length and 1 cm in diameter.

*Flower size.*—Average of 7 cm in diameter and 3.5 cm in depth.

*Flower quantity.*—Average of 5 per axillary node.

*Flower fragrance.*—Medium.

*Flower aspect.*—Outward.

*Petals.*—5 per flower, un-fused, not overlapping, obovate in shape, obtuse apex, round base, entire margin, average of 3.5 cm in length and 2 cm in width, color upper and lower surface when opening; a blend of 55A and 55B, color upper and lower surface when mature; slightly lighter than 65B, upper and lower surface is smooth and satiny.

*Sepals.*—5 per flower, 142A in color on upper and lower surface, pubescent surface, triangular in shape, entire margins, acuminate apex, base fused into tube, average of 1 cm in length and 2.5 mm in width with tube portion 1 cm in length and width.

*Pedicel.*—138A in color, average of 4 cm in length and 2.5 mm in width, surface is pubescent.

*Pistil.*—Compound carpel, stigmas; 4 fused at base, 1.25 cm in length, style; 2C and 8C in color, stigma; minute, ovary; pubescent, 149D in color.

*Stamens.*—Average of 16 per flower, anther; oblong in shape, 160B in color, filament; 1.25 cm in length and N57D in color, pollen; abundant in quantity and 4C in color.

*Position of stigmas relative to anthers.*—Primarily same level.

Fruit description:

*Shape.*—Round.

*Size.*—Average of 2.5 cm in diameter.

*Skin.*—At maturity; smooth surface with a thick glaucous coating, color a blend of 59A and 58A in color.

*Extent of anthocyanin overcolor of young fruit.*—Large.

*Fruit lenticels.*—Few, 0.3 mm in diameter and 162D in color.

*Flesh color.*—59A.

*Fruit presence.*—First visible in June in Manitoba, Canada, not retained through winter.

*Type of bearing.*—Primarily on spurs.

*Size of eye on fruit.*—An average of 4 mm.

*Length of fruit sepal.*—2 to 3 mm.

*Fruit area of russet around stalk attachment/eye basin.*—Absent or small.

*Length and width of the fruit stalk.*—3 cm in length and 2 mm in width.

*Depth and diameter of fruit cavity.*—Average of 4 mm in diameter and 2 mm in depth.

*Depth and width of the eye basin.*—2 mm in depth and width.

*Firmness of flesh.*—Very firm until frost.

*Apertures of locules in transverse.*—Closed to slightly open.

*Presence or absence of fruit calyx.*—Variable; sometimes retained but most often shed.

*Description of fruit crowning at the calyx end.*—Absent.

*Seed.*—Nearly renal-shaped, 4 to 5 per fruit, 1 per chamber, 5 mm in length and 2 mm in width, 170B in color.

It is claimed:

1. A new and distinct cultivar of crabapple tree named 'Jefnite' as herein illustrated and described.

* * * * *